United States Patent [19]
Ma et al.

[11] Patent Number: 6,162,362
[45] Date of Patent: Dec. 19, 2000

[54] DIRECT SCREW-ON CARTRIDGE HOLDER WITH SELF-ADJUSTABLE CONNECTION

[75] Inventors: Qi-Feng Ma; Fred Astani, both of Rancho Palos Verdes, Calif.

[73] Assignee: Phenomenex, Inc., Torrance, Calif.

[21] Appl. No.: 08/943,851

[22] Filed: Oct. 3, 1997

Related U.S. Application Data

[60] Provisional application No. 60/027,999, Oct. 8, 1996.

[51] Int. Cl.$^7$ .................................................. B01D 15/08
[52] U.S. Cl. ........................ 210/656; 210/198.2; 96/106
[58] Field of Search .............................. 210/198.2, 656; 210/232; 96/101, 106; 422/70

[56] References Cited

U.S. PATENT DOCUMENTS

| | | | |
|---|---|---|---|
| 4,026,803 | 5/1977 | Abrahams et al. | 210/198.2 |
| 4,173,363 | 11/1979 | Stearns | 258/177 |
| 4,181,853 | 1/1980 | Abu-Shumays et al. | 422/69 |
| 4,283,280 | 8/1981 | Brownlee | 210/198.2 |
| 4,451,363 | 5/1984 | Brownlee et al. | 210/198.2 |
| 4,451,364 | 5/1984 | Higgins et al. | 210/198.2 |
| 4,565,632 | 1/1986 | Hatch et al. | 210/656 |
| 4,888,112 | 12/1989 | Kronwald | 210/198.2 |
| 5,227,059 | 7/1993 | Shepherd | 210/198.2 |
| 5,338,448 | 8/1994 | Gjerde | 210/198.2 |
| 5,472,598 | 12/1995 | Schick | 210/198.2 |
| 5,482,628 | 1/1996 | Schick | 210/198.2 |

FOREIGN PATENT DOCUMENTS

| | | |
|---|---|---|
| 1120232 | 3/1982 | Canada . |
| 4326568 | 2/1995 | Germany . |
| 9505229 | 2/1995 | WIPO . |

OTHER PUBLICATIONS

PCT International Search Report dated Dec. 22, 1997.
Product catalog of Keystone Scientific, Inc., "Microbore Guard Columns," (Undated).
Product catalog of Alltech Associates, Inc., "Guard Columns," (Undated).
Product catalog of Upchurch Scientific, "Guard Cartridge Assemblies," (Undated).
Product catalog of Higgins Analytical, Inc., "Haiguard," (Undated).
Product catalog of Sarasep, Inc., "Standard and Micro Polymeric Columns Micro IC/HPLC," (Undated).
Product catalog of Waters Corporation, "Universal Guard Column Holder," (Undated).
Product catalog of Supelco, "Pelliguard Guard Columns, Superlguard Guard Columns," (Undated).
Product catalog of Phase Separations, Inc., "Guard Columns and Fittings," (Undated).

(List continued on next page.)

*Primary Examiner*—John Kim
*Attorney, Agent, or Firm*—Stetina Brunda Garred & Brucker

[57] ABSTRACT

A cartridge holder includes a holder body having a cavity along a longitudinal axis of the holder body. A floating screw has a longitudinal axis and a hole through the length of the floating screw. The floating screw is adapted to engage with the cavity in such a way that the floating screw is movable relative to the holder body along the longitudinal axis of the holder body. But rotary movement of the floating screw around the longitudinal axis of the holder body is confined by a restriction of the cavity. An outlet unit having a stem with a central hole and a length greater than that of the floating screw is adapted to be movably inserted into the hole of the floating screw, so that a first end of the outlet unit extends out of the hole and a second end of the outlet unit is engaged with the cavity. An end cap is provided to engage with the cavity. In use a cartridge is placed inside the cavity of the holder body between the end cap and the outlet unit. The floating screw can be screwed onto the endfitting by turning the holder body and, in the meantime, the outlet unit is pushed toward the endfitting so that a zero dead volume connection is achieved. Thus, the cartridge holder fits to all brands of column endfittings by self-adjusting the configuration of its connection unit. The cartridge holder also can be modified to connect a tubing directly to an endfitting.

51 Claims, 8 Drawing Sheets

OTHER PUBLICATIONS

Catalog of Metachem Technologies, Inc., "Safeguard Cartridge System," (Undated).

Catalog of The Perkin–Elmer Corporation, "Prolong Column Life with NewGuard Cartridges," (Undated).

YMC, Incorporated, "YMC–Pack Cartridge Guard Columns," (Undated).

Whatman, Inc., "HPLC Guard Cartridge System," (Undated).

Catalog of Optimize Technologies, Inc., "Optimize Innovations," (Undated).

DIRECT SCREW-ON CARTRIDGE HOLDER WITH SELF-ADJUSTABLE CONNECTION

This application claims the benefit under Title 35 USC 119(e) of U.S. provisional application No. 60/027,999 filed Oct. 8, 1996.

FIELD OF INVENTION

The present invention relates to a cartridge holder and connection for connecting a cartridge to a chromatography column.

BACKGROUND OF THE INVENTION

In the field of chromatography, such as high performance liquid chromatography (HPLC), gas chromatography (GC), supercritical fluid chromatography (SFC), and capillary electrochromatography (CEC), a cartridge is often installed in-line with a chromatography column. If the cartridge packing consists of the same material as the column packing, it is called a guard cartridge and protects the column from contamination. If the cartridge contains filtration material, the cartridge is a filter and functions to remove particulates from the mobile phase. The cartridge may also work as a sample concentrator, or as a solid phase derivatization device based on the properties of the cartridge packing. The cartridge may be constructed to have the shape of column, disk, or tubule. For installation of the cartridge in-line to a chromatography column, a cartridge holder is required. It is well established that dead volume in the connection between a tubing and a column inlet significantly affects the performance of the column. For example, the dead volume causes poor separation and peak broadening and overlap, and makes it very difficult to identify and quantify species in the sample, if not impossible. Those problems are even more serious when a small quantity of samples is involved. Although efforts have been made to minimize the dead volume by designing connection unions of different structures, it is not a easy job for an ordinary user to make a connection with minimal dead volume and great caution has to be taken during a connecting operation.

A conventional cartridge holder typically consists of three parts: inlet fitting 110, holder body 120, and outlet fitting 130 as depicted in FIG. 1. In this holder each end of tube 160 is separately connected to either column 180 or fitting 130. Cartridge 150 is secured in holder body 120 by fittings 110 and 130. Cartridge holder 100 is in-line connected to endfitting 170 of chromatography column 180 through tube 160 by finger tights 140. Since HPLC requires connections with minimal dead volume one must screw finger tight 140 and simultaneously press tube 160 against fitting 130 or 170 to ensure that the tube end is in close contact with the fitting. Obviously, this is an inconvenient process and runs the risk of generating dead volume during the connection. Another disadvantage is that, using two finger tights 140 for the connection between cartridge holder 100 and column 180, results in a long flow path for mobile phases, degrading column performance. Moreover, the two finger tights 140 have to be tightened separately and more time is needed to complete the connection.

Other cartridge holders include a two-piece cartridge holder of FIG. 2. The cartridge holder 200 has an end cap 210 and holder body 220. At the outlet side of the holder body 220, a threaded male coupling 221 with thin hole 222 extends out. Cartridge 250 is secured in body 220 by threading end cap 210 into holder body 220. To connect cartridge holder 200 onto chromatography column 280, the male coupling 221 of holder body 220 is screwed into endfitting 270 of column 280. Tapered section 223 is pressed against ferrule seat 271 of endfitting 270 to seal the connection. The pilot depth 272 of endfitting 270 is filled by pilot extension 224 of holder body 220 to reduce the dead volume of the connection. The two-piece cartridge holder can be directly screwed onto a chromatography column and that simplifies the connection process.

But the two-piece cartridge holder 200 has limitations. One major limitation is the compatibility of the holder connection. Many brands of column endfittings exist and each has a different configuration. Even if female thread 273 and ferrule seat 271 of endfitting 270 of column 280 are standardized, significant variation in the length of pilot depth 272 exists. If the length of pilot depth 272 of endfitting 270 is longer than the length of pilot extension 224 of cartridge holder 200, dead volume will be produced once cartridge holder 200 is screwed onto endfitting 270. If the length of pilot depth 272 of endfitting 270 is shorter than the length of pilot extension 224 of cartridge holder 200, tapered section 223 cannot be pressed tightly against ferrule seat 271, causing the connection to leak. This means that the two-piece cartridge holder 200 of defined pilot extension 224 can only be connected onto a column with the endfitting 270 of matched pilot depth 272. Moreover, most column users are not aware of the brand of the endfitting for the column they are using and often find it difficult to choose a suitable cartridge holder for the column. Further, small dimensional differences can exist that are not detectable visually, but which can greatly degrade performance.

Another cartridge is described in FIG. 3, in which the cartridge consists of two pieces. Inner piece 340 contains cartridge 341, tube 342, ferrule seat 343, and pilot depth 344. Outer piece 320 consists of female thread 321, cavity 322, channel 323, male thread 324, and tapered section 325. Inner piece 340 can move longitudinally in cavity 322 and channel 323.

For connection, cartridge holder 300 is screwed into endfitting 370 of column 380 and tightened to the extent that tapered section 325 of outer piece 320 is in contact with ferrule seat 371, but is not tight enough to grip and hold tubing 342 so that tubing 342 is still movable. The correct tightness is very difficult to achieve. A standard nut 310 with tubing 311 is then screwed into cavity 322 in cartridge holder 300 through female thread 321 and pushes inner piece 340 forward until the end of tube 342 of inner piece 340 reaches the bottom of pilot depth 372 of endfitting 370. A minimal dead-volume connection is supposed to be achieved in this way. Cartridge 300 is then firmly tightened to seal the connection with endfitting 370.

Though this design of FIG. 3 is supposed to match most column endfittings, it is not easy to determine how much tightening should be made in each step. For example, if cartridge 300 is tightened firmly to endfitting 370 before nut 310 screws in, then tube 342 of inner piece 340 will not move when nut 310 is threading in cartridge holder 300 and the end of tube 342 may be unable to move forward to fill pilot depth 372, thus increasing the dead volume. Further, tube 342 has a nonsupported portion 342a in cavity 322 of outer piece 320 to allow an adjustable range. Since sealing pressure from nut 310 is transferred entirely onto tube 342, a high sealing force is not acceptable for this design due to the possibility of breakage or deformation of the nonsupported portion 342a. Currently the design is believed only suitable for a miniaturized cartridge format.

When connecting a tubing to a chromatography column, similar problems as discussed above exist. In particular, it is difficult to achieve zero dead volume using conventional connecting union.

A cartridge holder with application multiplicity, column-fitting compatibility, and operation simplicity is needed.

SUMMARY OF THE INVENTION

One aspect of the present invention is to provide a cartridge holder which can automatically adjust the configuration of its connection unit to match different types of endfittings of chromatography columns, and achieve a zero dead-volume connection.

Another aspect of the present invention is to provide a cartridge holder which will accommodate different types of cartridges while retaining compatibility with different column endfittings.

Another aspect of the present invention is to provide a cartridge holder which can withstand high backpressure and is metal-free on its flow path.

Still another aspect of the present invention is to provide a connecting union which is compatible to different types of endfittings of chromatography columns with different pilot depth that can readily achieve a zero dead-volume connection.

A cartridge holder according to one aspect of the present invention includes a holder body having a cavity along a longitudinal axis of the holder body. A floating screw has a longitudinal axis and a hole through the length of the floating screw. The floating screw is adapted to engage with the cavity in such a way that the floating screw is movable relative to the holder body along the longitudinal axis of the holder body. But rotary movement of the floating screw around the longitudinal axis of the holder body is confined by the cavity. An outlet unit having a stem with a central hole and a length greater than that of the floating screw is adapted to be movably inserted into the hole of the floating screw, so that a first end of the outlet unit extends out of the hole and a second end of the outlet unit is engaged with the cavity. An end cap is provided to engage with the cavity. In use a cartridge is placed inside the cavity of the holder body between the end cap and the outlet unit.

A connection for connecting a tubing to an endfitting of a column according to one aspect of the present invention comprises a union body having a cavity along a longitudinal axis of the union body. A floating screw has a hole through the floating screw extending along a longitudinal axis of the floating screw is adapted to engage with the cavity in such a way that the floating screw is movable relative to the union body along the longitudinal axis of the union body. But rotary movement of the floating screw around the longitudinal axis of the union body is confined by the cavity. An end cap is adapted to engage with the cavity. The tubing is inserted through the end cap, the union body, and the floating screw, and has a positioning ferrule crimped thereon for engaging with the end cap. The connecting union may further comprise a stopper pad having a hole for receiving the tubing. The stopper pad is located inside the cavity to confine the floating screw.

According to another aspect of the present invention, an apparatus for forming a fluid connection with a chromatography column having an end fitting containing a pilot depth with a pilot seat comprises a housing. The housing has an aperture extending therethrough. The aperture has a first cavity with a restricted opening at one end of the cavity. A tube has a distal end extending through the restricted opening and has a proximal end with a radially enlarged portion that abuts the restricted opening to restrain axial motion of the tube relative to the housing in a direction toward the distal end of the tube. The proximal end of the tube is in fluid communication with the first cavity. A movable connector has an aperture through which the distal end of the tube extends a sufficient distance to allow the distal end to be placed against the pilot seat of the pilot depth of the chromatography column to place the tube in fluid communication with the column. The moveable connector is moveable along an axial length of the tube during installation. The moveable connector has a threaded portion adapted to threadingly engage the end fitting on the chromatography column. The moveable connector has a proximal end configured to engage a portion of the housing to restrain relative rotation of the housing and the moveable connector about a longitudinal axis of the tube.

According to another aspect of the present invention, an apparatus for forming a fluid connection with a chromatography column having an end fitting containing a pilot depth with a pilot seat comprises a housing. The housing has a cavity extending through the housing. The cavity having a ledge extending around an interior periphery of the cavity. The cavity has a first end through which fluid passes during use of the connector fitting. A tubular stem has a proximal end with a flange that cooperates with the ledge to restrain axial motion of the tubular stem relative to the housing along an axial length of the tubular stem in a direction toward a distal end of the tubular stem. The tubular stem has a distal end extending through a shaped opening in the housing. The proximal end of the tubular stem is in fluid communication with the fluid in the first end of the cavity. A movable connector has an aperture through which the distal end of the tubular stem extends a sufficient distance to allow the distal end to be placed against the pilot seat of the pilot depth of the chromatography column to place the tubular stem in fluid communication with the column. The moveable connector being moveable along an axial length of the tubular stem during installation. The moveable connector has a distal end threaded to engage the end fitting on the chromatography column. The moveable connector having a proximal end located in the cavity between the flange and the shaped opening with the proximal end of the moveable connector is configured relative to the shaped opening to permit movement of the moveable connector along the axial length of the stem but restrain rotation about that axial length so the moveable connector and the housing rotate together about that axial length.

According to another aspect of the present invention, an apparatus for use in connecting to a chromatography column having an end fitting containing a pilot depth having a pilot seat in fluid communication with the column comprises a housing having a cavity extending through the housing. There is provided means for placing the cavity in sealed fluid communication with a proximal end of a tubular stem and restraining motion of a proximal end of the stem relative to the housing along a longitudinal axis of the stem. There is provided means moveable relative to the housing and relative to the longitudinal axis of the stem for connecting a distal end of the stem to the end fitting and placing the distal end of the stem in sealed fluid communication with the pilot seat of the pilot depth. The housing has restriction means cooperating with the moveable means to cause the housing to rotate with the moveable means about the longitudinal axis of the stem.

According to the present invention, a method for forming a fluid connection with a chromatography column having an end fitting containing a pilot depth with pilot seat in fluid communication with the column comprises the steps of: (a)

placing a cavity in a housing in sealed fluid communication with a proximal end of a tubular stem, the stem having a longitudinal axis and a distal and proximal end; (b) restraining motion of the proximal end of a stem relative to the housing along a longitudinal axis of the stem in at least one direction; (c) placing the distal end of the stem against the pilot seat of the pilot depth; (d) moving a connector along the longitudinal axis to connect the distal end of the stem to the end fitting and to seal the distal end of the stem in fluid communication with the pilot seat of the pilot depth; and e) constraining the connector to rotate with the housing such that rotation of the housing causes the connector to move along the longitudinal axis.

A method for connecting a cartridge to a chromatography column according to one aspect of the present invention comprises the steps of: (a) providing a cartridge holder having a holder body with a cavity, a floating screw with a through hole, an outlet unit with a central hole, and an end cap; (b) placing the floating screw into the cavity of the holder body so that a first part of the floating screw is outside the cavity and a second part of the floating screw is inside the cavity, the second part is engaged with the cavity in such a way that turning the holder body will force the floating screw to turn accordingly, but the floating screw is free to move along a longitudinal direction of the cavity of the holder body; (c) inserting the outlet unit into the through hole of the floating screw, a first end of the outlet unit extending into the through hole and a second end of the outlet unit engaging with the cavity in such a way that allows independent movement of the floating screw relative to the outlet unit along a longitudinal axis of the holder body; (d) placing the cartridge into the cavity adjacent the second end of the outlet unit; (e) securing and tightening the end cap onto the cavity so that a flow passage is formed through the central hole, the cartridge, and the end cap, and that connections between the second end of the outlet unit and the cartridge, and between the cartridge and the end cap are sealed; and (f) screwing the first part of the floating screw into a column endfitting by turning the holder body while pushing the cartridge holder against the column endfitting.

The cartridge holder of the present invention has several advantages. The built-in male connection unit allows the cartridge holder to be directly screwed into the endfitting of a chromatography column without the need for additional connection units or adapters. The male connection unit can automatically adjust its configuration according to the structure of column endfitting, rendering the cartridge holder to be assembled onto any brand of column endfittings with zero dead volume connection. The male connection unit can be integrated to components other than cartridge holders for various applications requiring universal fitting and zero dead volume connection.

Similarly, the connecting union of the present invention can be used with different types of endfitting with different pilot depth, and to achieve zero dead volume automatically.

BRIEF DESCRIPTION OF THE DRAWINGS

The present invention will be better understood from the description of the embodiments given below, taken in conjunction with the drawings in which like reference characters or numbers refer to like parts throughout the description, and in which.

DETAILED DESCRIPTION OF THE PREFERRED EMBODIMENT

Figure 1:
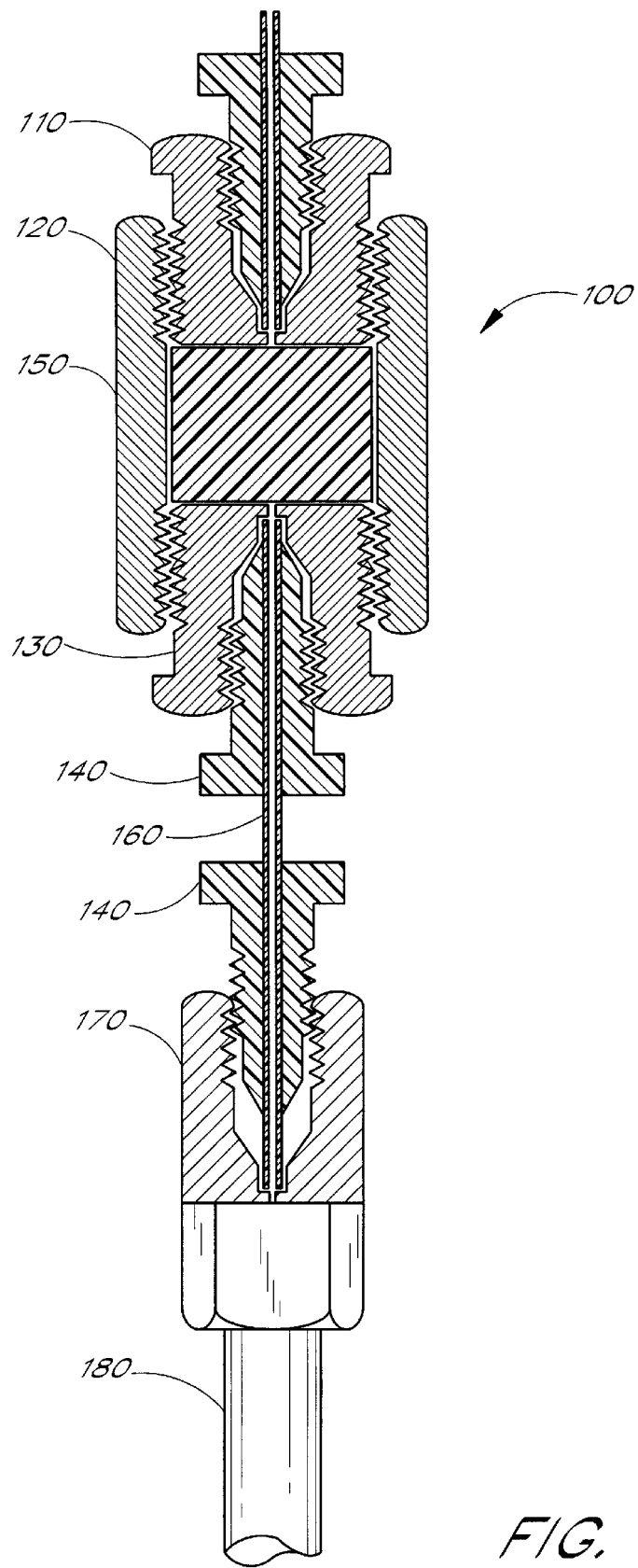
FIG. 1 shows a conventional cartridge of the prior art.
Figure 2:
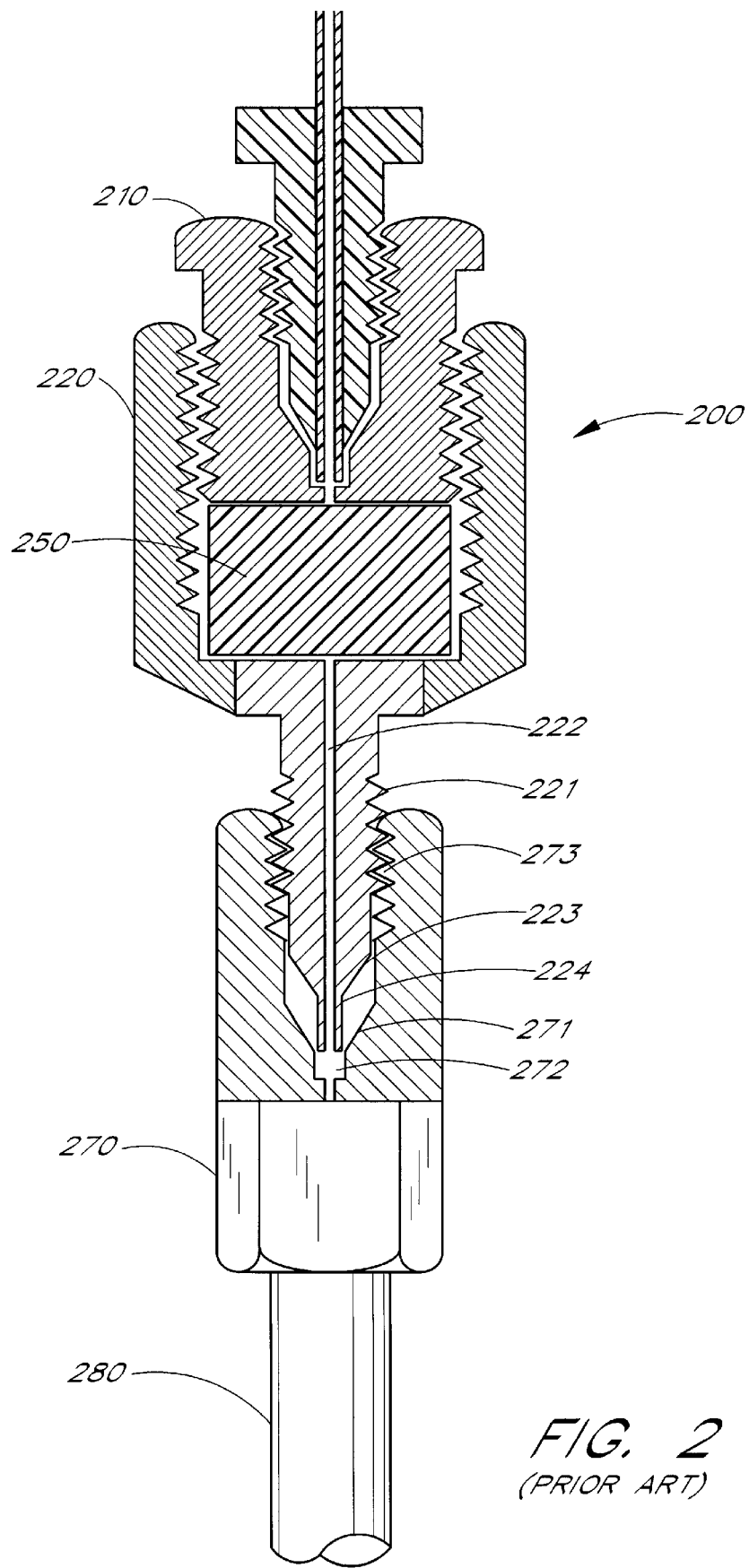
FIG. 2 shows a screw-on cartridge of the prior art.
Figure 3:
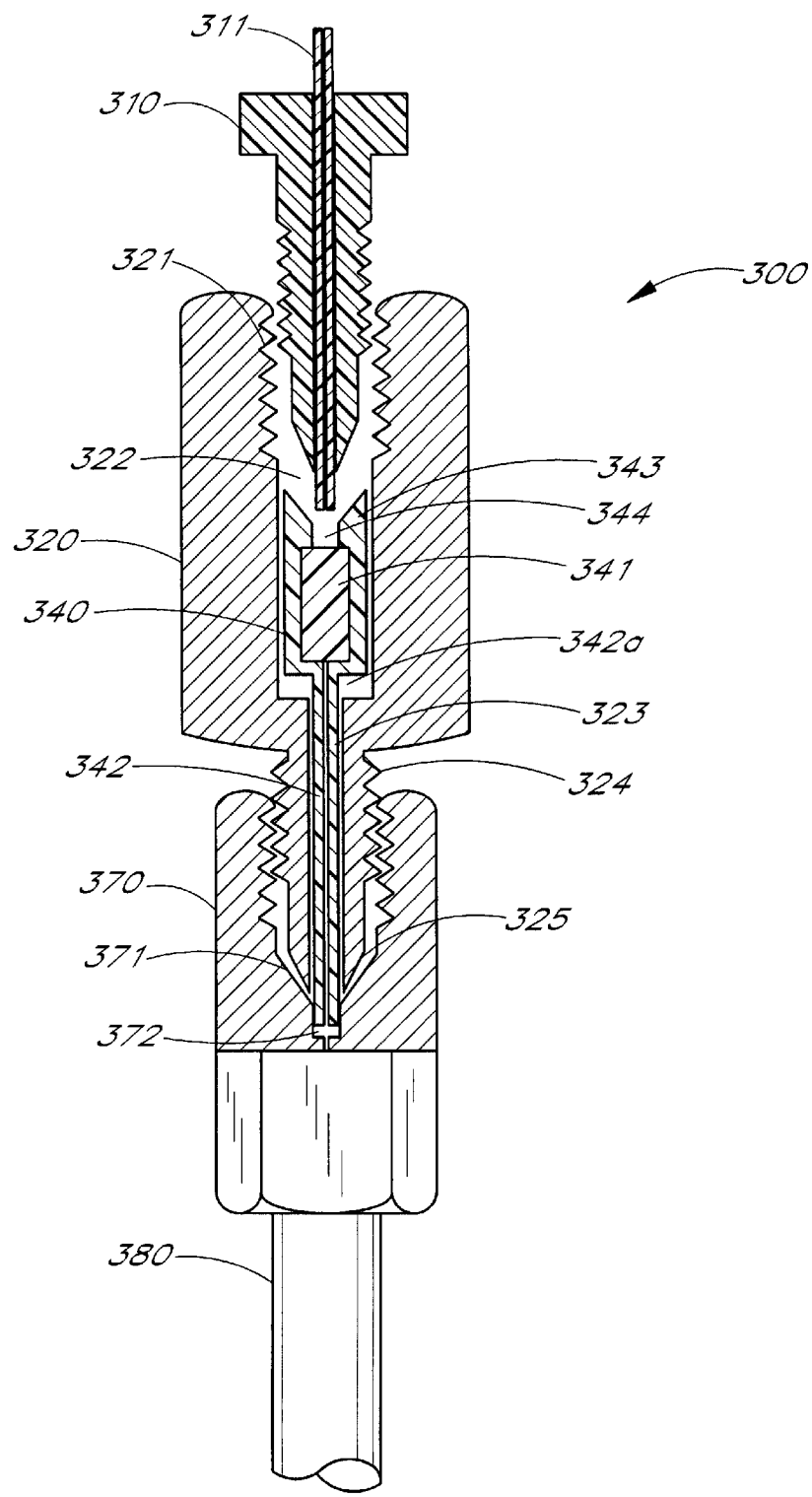
FIG. 3 shows a two-piece cartridge of the prior art.

In one embodiment of the present invention, the cartridge holder comprises a holder body, a floating screw, an outlet unit, and an end cap. A cartridge is held between the end cap and the outlet unit inside the cartridge body. Thus, the end cap, the cartridge, and the outlet unit are held together by the cartridge body, forming an in-line passage with a chromatography column. The floating screw serves to engage with the endfitting of the column and to secure and seal the outlet unit to the endfitting. One advantageous feature of the cartridge holder is that the floating screw is movable relative to the cartridge body in a direction along the longitudinal axis of the cartridge body and, in the meantime, engaged with the cartridge body so that the floating screw can be screwed on to the endfitting of a column by turning the cartridge body.

Through the engagement between the floating screw and the assembly of the cartridge body, the end cap, the cartridge, and the outlet unit, it is possible to keep the outlet unit in close contact with the full pilot depth of the column endfitting while tightening the floating screw to the endfitting. This is achieved in a simple manner. During a connection operation, in order to screw the floating screw on to the column endfitting and, in the meantime, to keep the outlet unit in close touch with the full pilot depth, the operator only needs to turn the cartridge body. By turning the cartridge body, the floating screw follows the rotary movement of the cartridge holder and is screwed on and, in the meantime, the outlet unit is automatically and naturally forced against the endfitting. The movement of the floating screw relative to the outlet unit allows the outlet unit stays in touch with the full pilot depth while the floating screw is moving toward the endfitting caused by turning the cartridge body. This relative movement also avoids any possible damage caused by unmatched pilot depth and outlet unit. Depending on the relative length of the floating screw and the outlet unit, it is possible that the outlet unit is not in touch with the bottom or pilot seat of the pilot depth of the endfitting at the beginning of a connecting operation. But as the turning of the holder body continues, the outlet unit will move toward the endfitting gradually and reach to the bottom of the pilot depth at certain point before the relative movement between the floating screw and the outlet unit is locked due to the squeeze of the floating screw or a ferrule on the outlet unit by the ferrule seat of the endfitting.

Based on the principle discussed above, there are other ways to assemble and configure the cartridge holder of the present invention.

As can be appreciated from the above discussion, to achieve zero dead volume the pilot seat of the pilot depth of the endfitting must be in close contact with the tubing or the pilot extension of a cartridge holder. By providing a structure allowing the relative movement between the floating screw and the outlet unit and, more importantly, allowing simultaneously the above relative movement and the movement of the floating screw toward the column endfitting through simple turning operation, the cartridge holder of the present invention is easy to operate to achieve a zero dead-volume connection and compatible to all types of column endfittings with different pilot depth. The cartridge holder can be used to accommodate different types of cartridges with different shapes to fulfill various functions, such as column protection, sample derivatization, sample preparation, sample concentration, and on-line eluent filtration. A modified version of the holder of the present invention can also be used as a zero dead-volume connection union for tubing installation.

The cartridge holder of the present invention is described in more detail below by reference to the drawings.

Figure 4A:
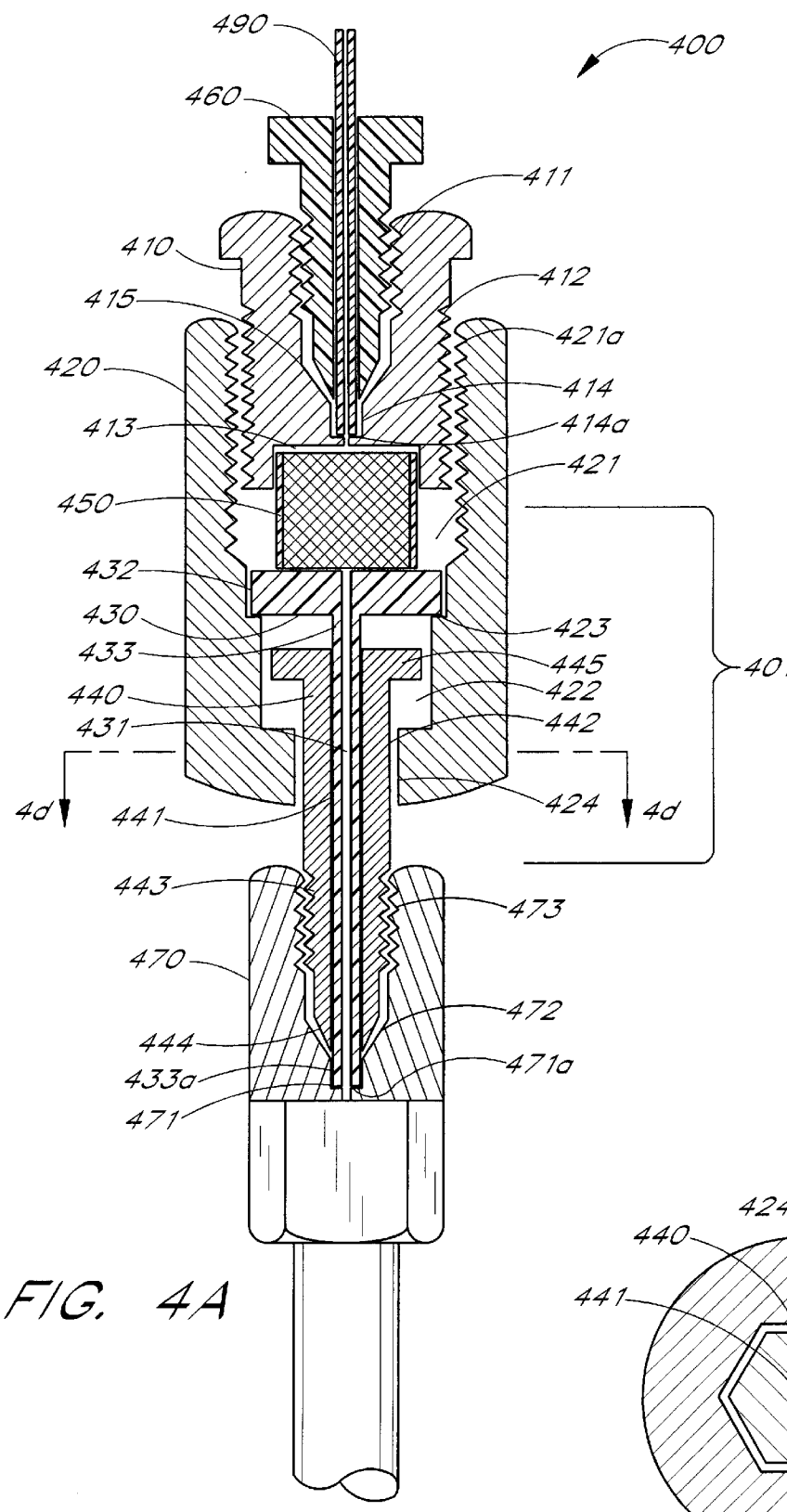
FIG. 4a shows an embodiment of the present invention.

FIG. 4a illustrates one embodiment of the cartridge holder of the present invention for cartridges with flat ends. A cartridge holder 400 comprises an end cap 410, a housing or holder body 420, an outlet unit 430 and a floating screw 440. In use, a cartridge 450 is placed in holder body 420 between end cap 410 and outlet unit 430. End cap 410 has a cylindrical female fitting 411, a cylindrical male thread 412, and a cavity 413. Female fitting 411 is of standard type for receiving a standard nut 460 with a tubing 490. Next to the unthreaded portion is a conical-shaped ferrule seat 415. At the narrow end of ferrule seat 415 is a cylindrical pilot depth 414. The diameter of pilot depth 414 matches that of tubing 490. At the end of pilot depth 414, there is a disk-shaped pilot seat 414a with a central hole thereon. Cavity 413 is located on the opposite side of female fitting 411 and communicates with female fitting 411 through the central hole of pilot seat 414a. Cavity 413 is for housing and holding cartridge 450 in position. Cavity 413 can have different shapes matching that of cartridge 450. Generally, cavity 413 has a side wall for confining cartridge 450 and an end surface for forming a radially sealed fluid passage with an end surface of cartridge 450. Male thread 412 is provided on the outer surface of end cap 410.

Cartridge 450 preferably has a side wall to hold and radially seal a packing material in the cartridge 450. Two end surfaces of cartridge 450 are open to fluid flow. When cartridge 450 is placed in holder body 420, one end surface is forced against the end surface of cavity 413. Thus, the conjunction between the end surface of cavity 413 and the end surface of cartridge 450 is sealed radially and a fluid passage is form between the two surfaces through the central hole 414a and the packing material of cartridge 450. Cartridge 450 can be made any shape acceptable by the cavity 413. In one embodiment, cartridge 450 has a cylindrical shape with two flat end (upper and lower) surfaces perpendicular to a cylindrical side wall. Accordingly, cavity 413 has a cylindrical side wall and a flat end surface perpendicular to the cylindrical wall, and the diameter of cavity 413 is slightly larger than that of cartridge 450. Under certain circumstances, the orientation of cartridge 450 may be important. For example, when a used but still usable cartridge is put back into cartridge holder 400, it is important to put it in the original orientation in order to prevent contamination to the column from the used part of the cartridge 450. Thus, cartridge 450 can be made to have different shapes at two sides and only one side matches the shape of cavity 413. It can be any shape as long as the two sides are different, such as circle, square, oval. It is also possible to provide a projection on side of the cartridge to prevent that side from entering cavity 413. Different color can be also used as indication.

Figure 4D:
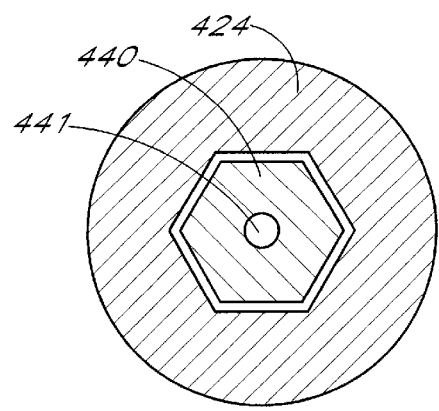
FIG. 4d is a cross-sectional view along 4d–4d of the cartridge holder of FIG. 4.

Housing or holder body 420 has a major cavity 421 and a smaller minor cavity 422 divided by an edge or ridge 423. At one end of holder body 420 is a restriction 424. Major cavity 421 has a female thread 421a extending about ⅔ into the major cavity 421 for engaging with male thread 412 of end cap 410. Minor cavity 422 is shorter and narrower than major cavity 421. The length of minor cavity 422 should be long enough to allow floating screw 440 to move relative to cartridge holder body 420 in a predetermined range so as to adapt to column endfittings with different pilot depths. Edge 423 forms at the conjunction of the two cavities 421 and 422. Edge 423 is configured to support outlet unit 430 when cartridge 450 is pushed against outlet unit 430 so that a good seal can be formed between cartridge 450 and outlet unit 430. In one embodiment, edge 423 has a flat surface substantially perpendicular to the axial direction of holder body 420. An aperture in one end of body 420 forms a restriction 424 designed to engage with floating screw 440. The cross-sectional area of restriction 424 matches that of floating screw and is slightly larger than the later, so that floating screw 440 can freely move through restriction 424 along a common longitudinal axis of both restriction 424 and floating screw 440. But rotary movement of floating screw 440 around the longitudinal axis is restricted by restriction 424 so that screw 440 rotates with holder body 420. Different types and shapes of apertures or restrictions 424 can be used. As long as the shaped opening of restriction 424 allows longitudinal movement of floating screw 440 but restrains rotation about the longitudinal axis. Thus, restriction 424 and the portion of floating screw 440 engaging the restriction 424 will typically have corresponding matching shapes that allow longitudinal movement but not relative rotation of the floating screw 440 and housing or holder body 420. In one embodiment, restriction 424 is a hexagonal channel (as shown in FIG. 4d) and its internal diameter is smaller than the internal diameter of minor cavity 422. Restriction 424 can also be made of a cylindrical shape with slots extending along its longitudinal axis to pin floating screw 440. Restriction 424 should be long enough to rotate and direct the forward and backward movement of floating screw 440 to avoid tilting. There is thus advantageously provided a means for rotating holder body 420 and floating screw 440 together while allowing floating screw 440 to move along the longitudinal axis of floating screw 440 relative to holder body 420. There is also advantageously provided means for restraining rotation of the floating screw 440 relative to the holder body 420 while permitting relative movement along the longitudinal axis of floating screw 440.

Floating screw 440 has a stem 442 extending from a head or limiting rim 445, a male thread 443 is formed on the exterior of stem 442. The stem 442 ends in a tapered tip 444. A channel 441 extends through head 445 and stem 442. Channel 441 is for accommodating outlet unit 430, which can be any appropriate shape as long as it matches with the shape of outlet unit 430. In one embodiment, Channel 441 is cylindrical and has an internal diameter slightly larger than the outer diameter of tail 433 of outlet unit 430. The length of channel 441 should be shorter than the length of tail 433 so that tail 433 can extend out from channel 441 if assembled according to FIG. 4. The difference in length between channel 441 and tail 433 determines the pilot depth to which the cartridge holder is compatible. Preferably, the difference in length is made larger than the largest pilot depth of a column intended to be connected with the cartridge holder so that one end of tail 433 can be made in touch with the bottom of the pilot depth of the column when floating screw is screwed onto the endfitting of the column.

Accordingly, minor cavity 422 of holder body 420 preferably has a length at least equal to the difference between stem 433 of outlet unit 430 and channel 441 of floating screw 440. Stem 442 extends from the head or limiting rim 445 to thread 443 and is designed to engage with restriction 424. Thus, stem 442 has an exterior shape matching with the shape of restriction 424 and has a cross-sectional area slightly smaller than the internal cross-sectional area of restriction 424 of holder body 420. In one embodiment, stem 442 has a hexagonal shape cross-sectionally. In another embodiment, stem 442 has a cylindrical shape with projections extending along its longitudinal axis. The projections match the slots on restriction 424. Limiting rim 445 is optional, it has a cross-sectional area larger than the internal cross-sectional area of restriction 424. When constructed as in FIG. 4, limiting rim 445 functions to keep floating screw 440 from falling off. Floating screw 440 also has a tapered tip 444. Tip 444 preferably has a conical shape matching the shape of a ferrule seat 472 of an endfitting 470.

Outlet unit 430 has a hole 431 extending through a head 432 and a tail 433. Hole 431 defines a passage for fluid to flow therethrough. In one embodiment, head 432 has a disk shape with a diameter close to the internal diameter of major cavity 421 and can be press-fitted in major cavity 421. One side of head 432 is supported by edge 423 of holder body 420. The other side of head 432 has a flat surface. The flat surface supports one end surface of cartridge 450 and forms a radially sealed connection between these two surfaces when cartridge 450 is forced against head 432. Structures other than a flat surface also can be used for head 432 as long as it matches with the shape of the end surface of cartridge 450. Major cavity 421 and minor cavity 422 are thus separated by head 432. Head 432 restrains movement of stem 433 along the axial length of stem 433, and advantageously only in the direction of the distal end of stem 433 that abuts pilot seat 471a. Any suitable means of restraining the axial motion can be used, including conventional ferrules and seats. Head 432 can be of different shapes and made of suitable rigid material, such metal and plastic. Tail 433 can also be constructed of any suitable rigid material, such as metal and plastic. In another embodiment, it is also possible to build outlet unit 430 and holder body 420 into an integral structure that is simultaneously formed from a single material. Preferably, tail 433 has a tip with a flat surface substantially perpendicular to the longitudinal axis of tail 433 which can brought in close contact with a pilot seat 471a of endfitting 470. Thus, tail 433 is inserted into the full length of a pilot depth 471 of endfitting 470, and hole 431 of outlet unit 430 is connected to a central hole of pilot seat 471a and forms a radially sealed fluid passage. Optionally, the tip of tail 433 is provided with a ferrule.

Holder body 420, outlet unit 430, and floating screw 440 are preferably assembled into one assembly during manufacture. Tail 433 of outlet unit 430 is inserted into channel 441 of floating screw 440, and they are positioned into minor cavity 422 from major cavity 421 and secured by press head 432 of outlet unit 430 against edge 423 of body 420. The finished product will contain two units: end cap 410 and the assembled female unit 401. Cartridge 450 can be installed into cartridge holder 400 simply by placing the cartridge in cavity 413 of end cap 410 and screwing the female unit 401 onto the end cap.

One of the advantages of the present invention is that cartridge holder 400 can be screwed into the endfitting of a chromatography column directly to provide a shorter flow path, and is compatible with all types of column endfittings. To install cartridge holder 400 into a chromatography column, male thread 443 of floating screw 440 is engaged with female endfitting 470 of column 480. Floating screw 440 will be automatically pressed back against head 432 of outlet unit 430 by the engagement and tail 433 of outlet unit 430 will be exposed to its maximum extent. Since rotational movement of floating screw 440 against holder body 420 is prohibited by the engagement with restriction 424 of holder body 420, floating screw 440 is threaded into endfitting 470 of column 480 by turning cartridge holder 400. Floating screw 440 and tail 433 of outlet unit 430 are moving in parallel towards the column 480 during threading until the distal end 433a of tail 433 reaches the bottom (i.e. pilot seat 471a) of pilot depth 471 of endfitting 470. Further threading will pull floating screw 440 towards the endfitting 470, but tail 433 of outlet unit 430 will not move as it slides within channel 441.

When tapered tip 444 of floating screw 440 is pressed against ferrule seat 472 of endfitting 470, it deforms radially inward toward tail 433 to hold and seal tail 433 of outlet unit 430 into column endfitting 470.

As described above, full length of pilot depth 471 of column endfitting 470 is filled by the distal end 433a of tail 433 of outlet unit 430 with the threading process and no dead volume is generated in the junction between distal end 433a of tail 433 and pilot depth 471 of column endfitting 470. Since floating screw 440 can move back and forth along the length of tail 433 of outlet unit 430, the length of distal end 433a of tail 433 is self-adjusted to fit different types of pilot depth 471 of endfitting 470, ensuring zero dead volume connection.

There is thus advantageously provided an elongated and adjustable floating member 440 having a distal end sealingly connected to column 480 and a proximal end movably connected to cartridge holder body 420. A tubular member 433 extends through the member 440 and is movable relative to member 440 until a distal end 433a of member 433 is sealed in fluid communication with column 480 by the distal end of member 440. A proximal end of member 433 is in sealing engagement with holder body 420 and in fluid communication with a cartridge 450 contained in body 420.

The tubular member 433 thus has a proximal end in fluid communication with cartridge 450 and sealed to body 420 containing cartridge 450. The distal end of member 433 moves relative to floating member 440 as the member 440 engages endfitting 470 and urges the distal end 433a of member 433 against the pilot seat 471a until the distal end 444 of floating member 440 engages ferrule seat 472 to form a seal with ferrule seat 472 and with the distal end 433a. This places the distal end 433a in sealed fluid communication with column 480.

The cartridge holder of the present invention may be made of metal for optimum strength or be made of rigid plastic for biocompatibility. It may also be made of a combination of rigid plastic and metal to achieve both biocompatibility and maximum strength. The holder for this purposes should be constructed so that all parts with thread be made of metal and all parts with flow channel be made of rigid plastic. Holder body 420 and floating screw 440 is preferably made of metal. Outlet unit 430 is preferably made of rigid plastic.

Given the above disclosure, many modifications can be made to the basic design described in FIG. 4 and there follows a few examples. To prevent materials leaking out from a cartridge into the flow line, a frit may be placed at the upstream opening of hole 431 on head 432 of outlet unit 430. When an extremely narrow flow channel is required and the one-piece outlet unit 430 cannot be made with such a narrow hole, tail 433 can be replaced by a piece of ready-made narrow tubing and the tubing can be permanently fixed onto head 432 of outlet unit 430 by any means applicable. To avoid possible bending during connection, tail 433 may have a protective sleeve at the section close to head 432. For better sealing, tapered tip 444 can have various shapes or can be replaced by ferrules of different type.

Figure 4B:
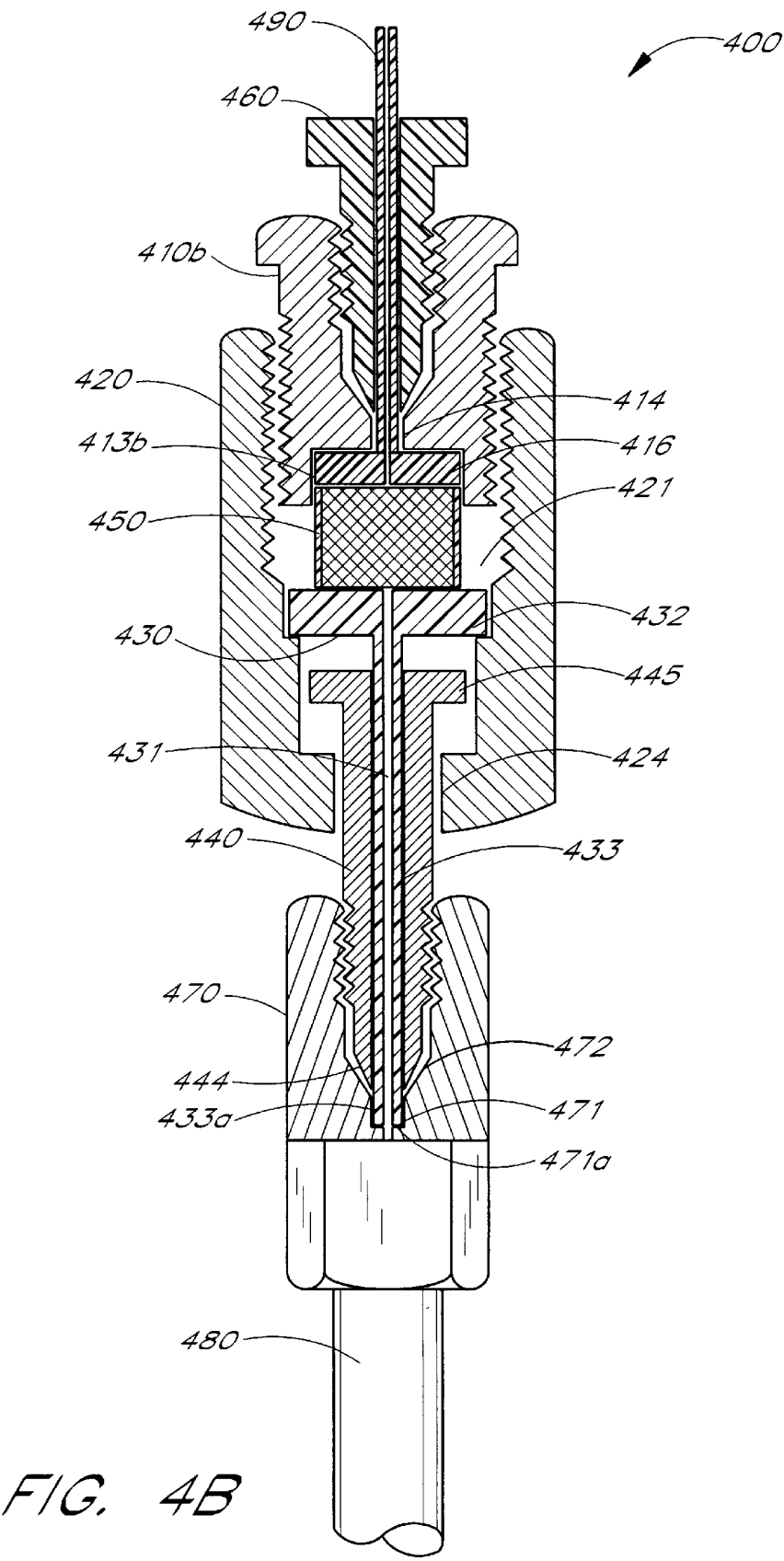
FIG. 4b shows another embodiment of the present invention.

Referring to FIG. 4b, end cap 410b is modified in this embodiment. End cap 410b is made of metal and is structurally the same as end cap 410 in FIG. 4a except that cavity 413b is deepened or lengthened along the longitudinal axis of holder 400 so pilot depth 414 opens directly into cavity 413b. A nonmetal pad 416 is then press-fitted into the closed end of cavity 413b. The tiny hole at the center of pad 416 aligns with the hole in inlet tubing 490. Mobile phase will flow from inlet tubing 490 into the hole of pad 416, pass through cartridge 450, and exit out of outlet unit 430 through hole 431 in tail 433. No metal is used in the whole flow path. Thus, no metal will be exposed to the fluid flowing in the flow path. The ability to insulate the mobil phase from contact with metal is advantageous in some circumstances.

Figure 4C:
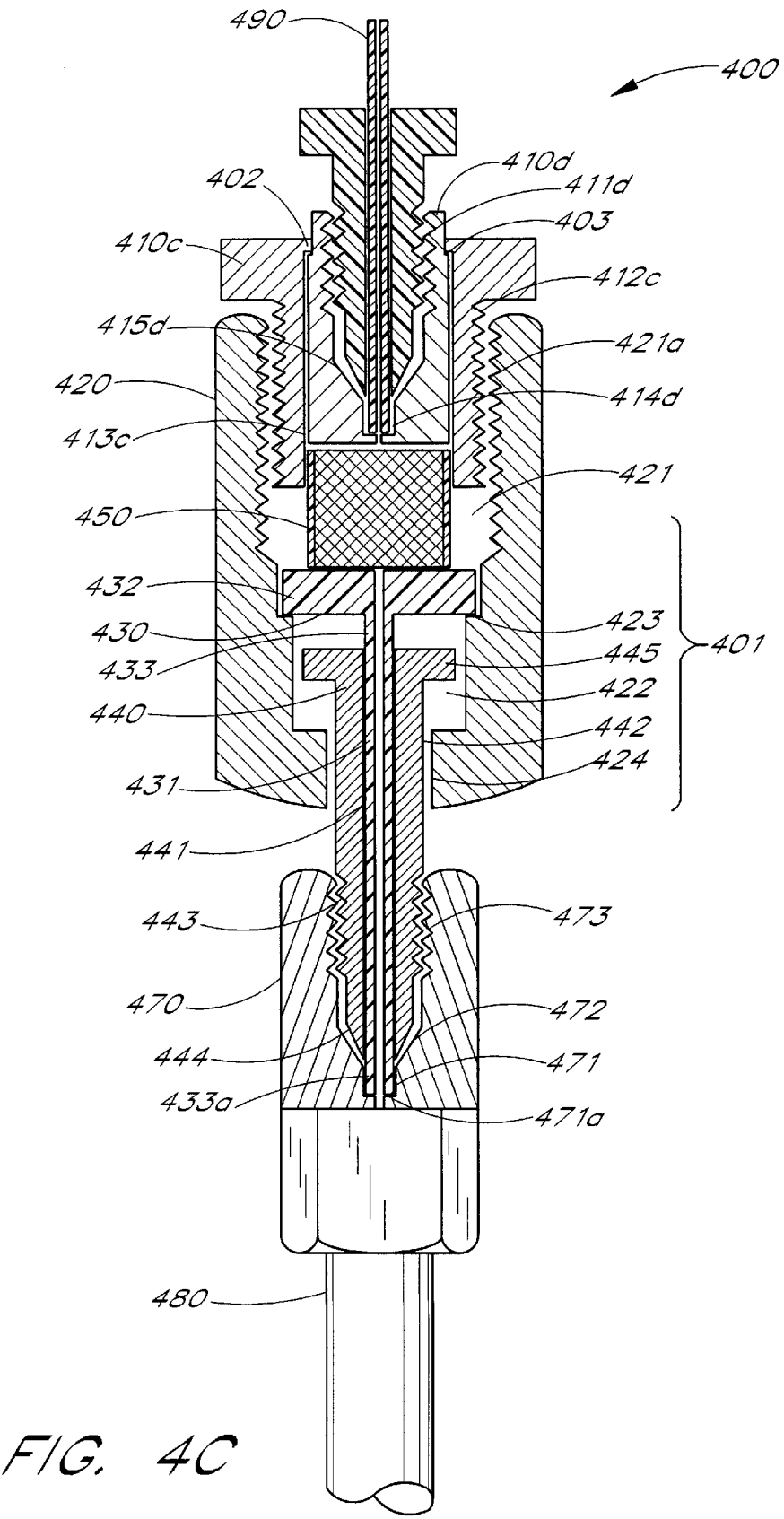
FIG. 4c shows a cartridge with a movable center unit in another embodiment of the present invention.

FIG. 4c shows another embodiment of the cartridge holder of the present invention. As can be appreciated from the discussion regarding the prior cartridge holder 400, shown in FIG. 4a, in order to form a nonleaking flow path between end cap 410, cartridge 450, and outlet unit 430, a sufficiently large force is needed to keep these three parts sealed together. The relatively large cross-sectional area of cartridge 450 makes it more demanding to apply the sealing face. When end cap 410 is screwed on against cartridge 450, the rotary movement of end cap 410 will directly act on the surface of cartridge 450 which is in contact with the bottom surface of end cap 410. This twisting force may damage the cartridge. Thus, a modified end cap is used in the cartridge holder shown in FIG. 4c. The end cap comprises two part: an annular end cap body 410c and a movable center unit 410d. End cap body 410c has a male thread 412c on its outer surface for engaging with female thread 421a of cartridge holder 420. End cap body 410c also has a hole or cavity 413c for receiving center unit 410d and cartridge 450. At the end of hole 413c opposite to cartridge 450, there is a flange, lip, or stopper 402 to confine center unit 410d along the longitudinal axis of the holder 400. In one embodiment, stopper 402 forms a cylindrical flange with a diameter smaller than that of hole 413c and smaller than the exterior of the center unit 410d contained in cavity 413c. Center unit 410d has a female fitting 411d, a ferrule seat 415d, and a pilot depth 414d. Center unit 410d has a outer diameter slightly smaller than the inner diameter of hole 413c so that it can be slidably inserted into hole 413c. The outer surface of center unit 410d has a step or shoulder 403 for engaging with stopper 402.

In use, center unit 410d is inserted into end cap body 410c. Body 410c is then screwed into cavity 421. By tuning end cap body 410c, center unit 410d is forced against cartridge 450 through the engagement between stopper 402 and step 403. Thus, the twisting force acting on cartridge 450 is significantly reduced. The other parts of the cartridge holder of FIG. 4c are the same as that of FIG. 4a and they share same reference numbers.

Figure 5:
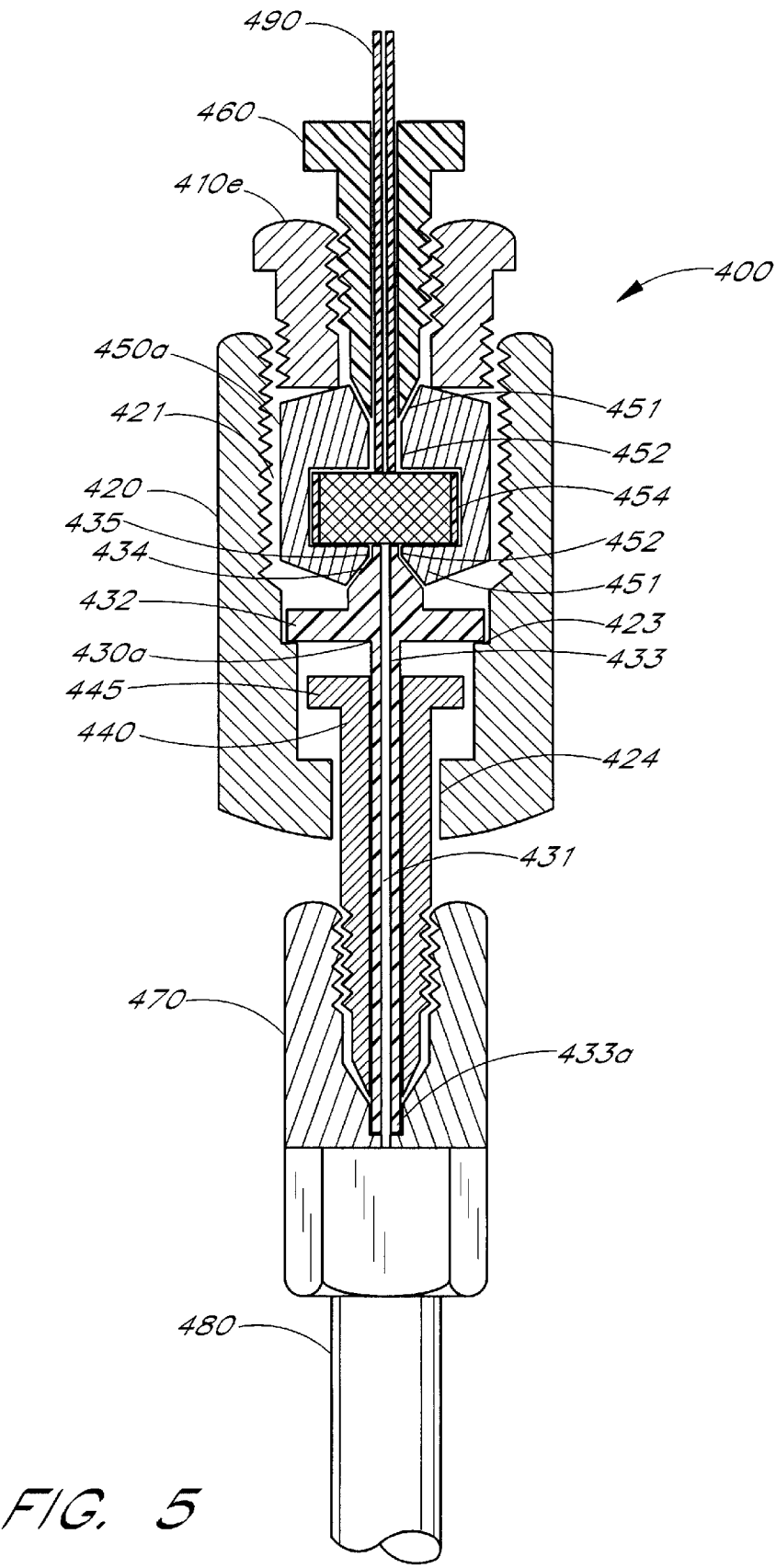
FIG. 5 shows a cartridge containing a ferrule seat in another embodiment of the present invention.

FIG. 5 describes another embodiment of the cartridge holder of the present invention for cartridges containing ferrule seats on their ends. As shown cartridge 450a has a ferrule seat 451 on each side extending to a pilot depth 452. Cartridge packing material 454 is contained in the cartridge 450a by a side wall and two end surfaces. In one embodiment, the side wall has a cylindrical shape, and each of the two end surfaces has a conical shape concentric with ferrule seat 451. End surfaces with other shapes can also be used with cartridge 450a, such as flat end surface. To accommodate cartridges of this type, end cap 410 and outlet unit 430 of the cartridge holder described in FIG. 4a are modified. For end cap 410, cavity 413 is deepened beyond ferrule seat 415 in FIG. 4a to form the modified end cap 410e (FIG. 5). For outlet unit 430a, an additional male fitting unit containing a tapered shoulder 434 and a pilot extension 435 is provided extending out of head 432 of outlet unit 430 as shown in FIG. 5.

For installation, cartridge 450a is positioned in cavity 421 and tapered shoulder 434 of outlet unit 430a is engaged to ferrule seat 451 of cartridge 450a. Inlet tubing 490 is inserted all the way into pilot depth 452 of cartridge 450a to abut cartridge 450a, and is sealed and held in position by tightening finger nut 460, as illustrated in FIG. 5. The cartridge holder 400 containing the cartridge can be screwed onto a column 480 in the same way as described for the embodiment in FIG. 4. Since no changes are made to the connection unit of the cartridge holder 400, the column endfitting compatibility is retained as described relative to FIG. 4a.

Figure 6:
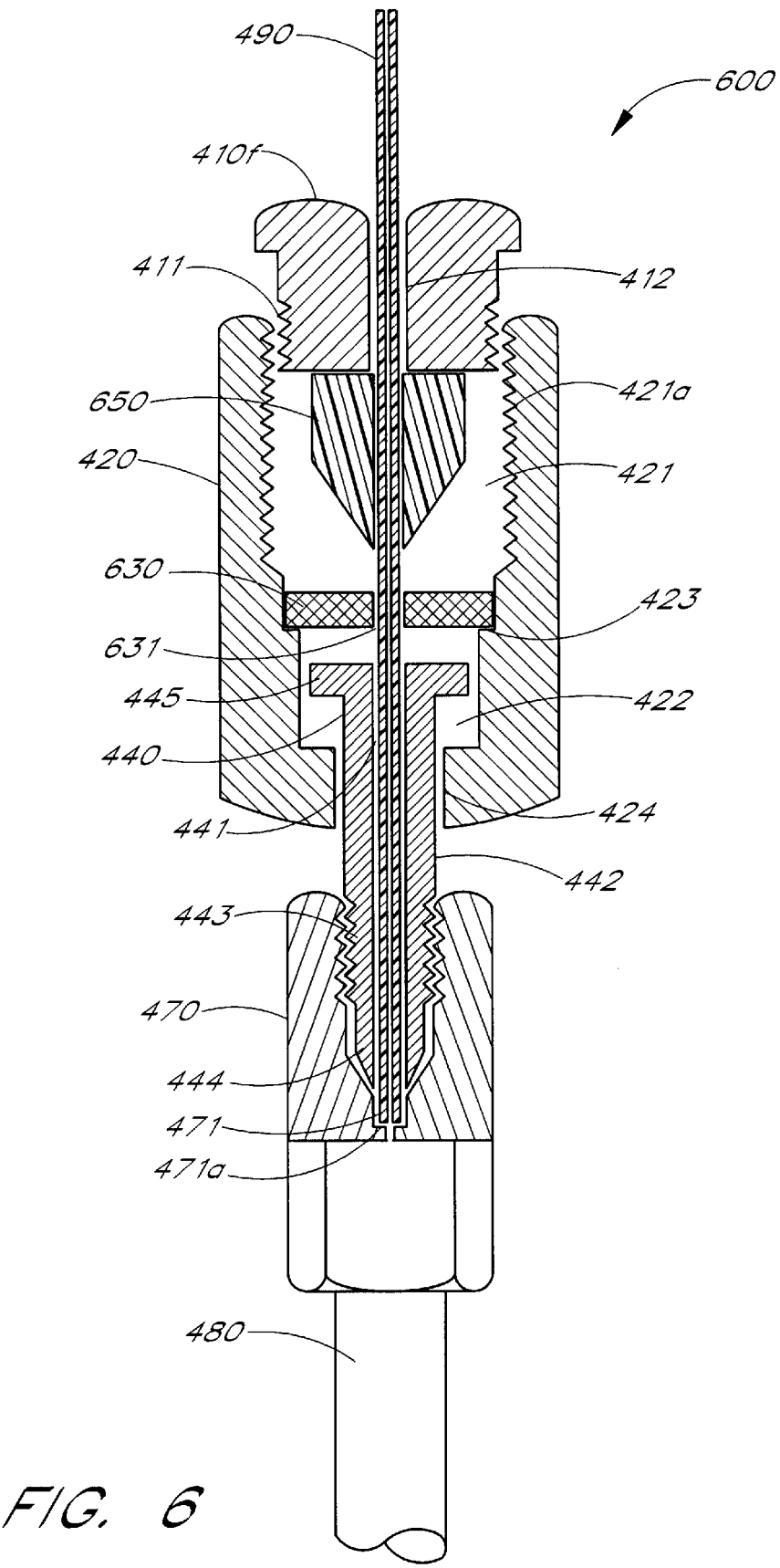
FIG. 6 shows a connecting union for connecting a tubing to a column inlet in another embodiment of the present invention.

FIG. 6 shows a further embodiment of the present invention. Connecting union 600 comprises an end cap 410f, a union body 420, a stopper 630, and a floating screw 440. A ferrule 650 is crimped onto a tubing 490 to be connected to an endfitting 470 of a column 480. Ferrule 650 should be able to be fixed at a predetermined position of tubing 490. Preferably, ferrule 650 is made of metal although rigid plastics also can be used. End cap 410f, which is similar to end cap 410e of FIG. 5 and can be made of metal or rigid plastic, has an external male thread 411 and a hole 412 through its longitudinal axis. Preferably, hole 412 is a cylindrical hole, although other shape also can be used. The internal diameter of hole 412 is bigger than the outer diameter of tubing 490 which extends through the hole 612.

In this embodiment, the outlet unit 430 of FIG. 4 is replaced with stopper 630 and the channel 441 of the floating screw 440 is sized to accommodate the passage of tubing 490. Stopper 630 rests on shoulder or edge 423 and contains a hole 631 to allow passage of tubing 490.

The length of the tubing 490 from ferrule 650 should at least equal to the sum of the length of channel 441, the thickness of stopper 630, and the pilot depth, so that tubing 490 can be placed against the bottom (i.e. pilot seat 471a) of the pilot depth 471 of the endfitting 470 while floating screw 440 is screwed onto the endfitting 470 of the column 480 as previously described.

Stopper 630 has a concentric hole 631 aligned with hole 412 for receiving tubing 490. Stopper 630 can be made of metal, plastics, and other suitable material. Preferably, stopper 630 is a metal pad of disk shape. In one embodiment, the outer diameter of stopper 630 is the same as or slightly larger than the internal diameter of a major cavity 421 of the union body 420, so that stopper 630 can be inserted into major cavity 421 and holds itself in position by friction force or a press fit. the outer diameter of stopper 630 can also be made slightly smaller than that of major cavity 421. Other mechanism also can be used to secure stopper 630 in position. The movement of floating screw 440 thus is confined by stopper 630 at one end of minor cavity 422.

Body 420, stopper 630, and floating screw 440 are preferably assembled into one assembly during manufacture. Briefly, floating screw 440 is placed into minor cavity 422 of union body 420 and confined inside minor cavity 422 by pressing stopper 630 against edge 423. To assemble tubing 490 with ferrule 650 into body 420, tubing 490 is inserted into major cavity 421 of body 420, then passes through hole 631 of stopper 630, and exits through channel 441 of floating screw 440 as illustrated in FIG. 6. End cap 410ƒ is then screwed into body 420 to trap ferrule 650 in major cavity 421. In one embodiment, thread 411 of end cap 410ƒ have a length so determined that when it is threaded to its end, ferrule 650 can rotate freely inside major cavity 421, but not move axially along tube 490. To connect tubing 490 onto a column 480, male thread 443 of floating screw 440 is screwed onto endfitting 470 of column 480 by turning body 420. In the meantime, tubing 490 is pushed toward the endfitting 470 by body 420 because the movement of ferrule 650 in one direction along the longitudinal axis is prohibited by end cap 410ƒ and tubing 490 is positionally fixed into ferrule 650. While body 420 can rotate around ferrule 650 and tubing 490, floating screw 440 is threaded into endfitting 470 of column 480 by turning body 420. The mechanism for self-adjustable fitting and connection procedure are the same as that for the cartridge holder described in FIG. 4.

For conventional connections using a finger tight as described in FIG. 1, one has to constantly press the tubing to fill the pilot depth of the endfitting while simultaneously screwing the finger tight into the endfitting. This is an inconvenient process with high risk of generating dead volume. After just a few times of tightening and loosening, the tip of the finger tight is narrowed and the process becomes more difficult. If the connection is done by the holder described in FIG. 6, one only needs to turn the holder and zero dead-volume connection is automatically achieved.

Many modifications and variations of the cartridge holder described above may be made without departing substantially from the spirit and scope of the present invention. Accordingly, it should be clearly understood that the form of the invention described and illustrated herein is exemplary only, and is not intended as a limitation on the scope.

What is claimed is:

1. A cartridge holder comprising: a holder body having a cavity along a longitudinal axis of the holder body;
   a floating screw having a hole through the length of the floating screw, the screw being adapted to engage with said cavity in such a way that the floating screw is movable relative to said holder body along said longitudinal axis of said holder body, but with rotary movement of said floating screw around said longitudinal axis of said holder body being confined by said cavity; and
   an outlet unit having a stem with a central hole and a length greater than that of the floating screw, and adapted to be movably inserted into said hole of said floating screw so that a first end of said outlet unit extends out of said hole and a second end of said outlet unit is engaged with said cavity.

2. A cartridge holder of claim 1, further comprising an end cap adapted to engage with said cavity and a cartridge removably placed in said cavity adjacent said second end of said outlet unit, wherein said end cap pushes said cartridge against said second end of said outlet unit so as to form a fluid passage through said central hole of said outlet unit, said cartridge, and said end cap.

3. A cartridge holder of claim 1, further comprising an end cap adapted to engage with said cavity, wherein said end cap comprises an end cap body for engaging with said holder body and a center unit for receiving an inlet unit, said end cap body has a seat for receiving said center unit and restricting movement of said center unit in one direction along a longitudinal axis of said end cap.

4. A cartridge holder of claim 1, wherein a first portion of said cavity has a cylindrical shape and at least a part of said first portion is threaded for receiving an end cap adapted for engaging said cavity, a second portion of said cavity has a cylindrical shape with a diameter smaller than that of said first portion and is separated from said first portion by a first step structure forming a first edge, said outlet unit has a head at said second end adapted to engage with said edge, said head has a disk shape with a diameter slightly smaller than that of said first portion, but larger than that of said second portion, and wherein a third portion of said cavity comprises a hexagonal channel with a cross-sectional area smaller than that of said second portion of said cavity and is separated from said second portion by a second step structure forming as second edge, and part of said floating screw has a hexagonal shape matching and engaging with said hexagonal channel of said cavity.

5. A cartridge holder of claim 4, wherein said floating screw has a rim at one end, said rim is located in said second portion of said cavity when in use and has a cross-sectional area larger than that of said hexagonal channel of said third portion so as to keep said floating screw from falling off said cavity.

6. A cartridge holder of claim 2, further comprising a plastic pad placed between said cartridge and said end cap and forming part of said fluid passage, wherein material exposing to said fluid passage is nonmetal material.

7. A cartridge holder of claim 2, wherein said cartridge has a first side facing said end cap and a second side facing said outlet unit, and said first and second side has different color.

8. A cartridge holder of claim 2, wherein said cartridge has a first side facing said end cap and a second side facing said outlet unit, and said first and second side has different shape.

9. A cartridge holder of claim 8, wherein said end cap has a cavity for receiving said cartridge and a first side of said cartridge has a shape matching that of said cavity of said cartridge.

10. A connection for connecting a tubing to an endfitting of a chromatography column comprising:
    a union body having a cavity along a longitudinal axis of the body;
    a floating screw having a hole through the floating screw extending along a longitudinal axis of the floating screw, and adapted to engage with said cavity in such a way that the floating screw is movable relative to said union body along said longitudinal axis of said union body, but rotary movement of said floating screw around said longitudinal axis of said union body is confined by said cavity;
    an end cap adapted to engage with said cavity;
    wherein said tubing is inserted through said end cap, said union body, and said floating screw, and said tubing has a positioning ferrule crimped thereon for engaging with said end cap.

11. A connection of claim 10, further comprising a stopper pad having a hole for receiving said tubing, and said stopper pad is located inside said cavity to prevent said floating screw from moving along the longitudinal axis toward said end cap.

12. A connection of claim 11, wherein a first portion of said cavity has a cylindrical shape and at least a part of said first portion is threaded for receiving said end cap, a second portion of said cavity has a cylindrical shape with a diameter smaller than that of said first portion and is separated from said first portion by a first step structure forming a first edge, said stopper pad has a disk shape and is secured to said first edge.

13. A connection of claim 12, wherein a third portion of said cavity comprises a hexagonal channel with a cross-sectional area smaller than that of said second portion of said cavity and is separated from said second portion by a second step structure forming a second edge, and part of said floating screw has a hexagonal shape matching and engaging with said hexagonal channel of said cavity.

14. A connection of claim 13, wherein said floating screw has a rim at one end, said rim is located in said second portion of said cavity when in use and has a cross-sectional area larger than that of said hexagonal channel of said third portion so that said rim of said floating screw is confined between said second edge and said stopper pad.

15. An apparatus for forming a fluid connection with a chromatography column having an end fitting containing a pilot depth with a pilot seat, comprising:
  a housing having an aperture extending through the housing, the aperture having a first cavity with a restricted opening at one end of the cavity;
  a tube having a distal end extending through the restricted opening and having a proximal end with a radially enlarged portion that abuts the restricted opening to restrain axial motion of the tube relative to the housing in a direction toward the distal end of the tube, the proximal end of the tube being in fluid communication with the first cavity;
  a movable connector having an aperture through which the distal end of the tube extends a distance sufficient to allow the distal end to be placed against the pilot seat of the pilot depth of the chromatography column to place the tube in fluid communication with the column, the moveable connector being moveable along an axial length of the tube during installation, the moveable connector having a threaded portion adapted to threadingly engage the end fitting on the chromatography column, the moveable connector having a proximal end configured to engage a portion of the housing to restrain relative rotation of the housing and the moveable connector about a longitudinal axis of the tube.

16. An apparatus as defined in claim 15, wherein the distal end of the moveable connector has a tapered portion that engages a tapered portion in the end fitting to move the distal end of the moveable connector toward the tube to seal the distal end of the tube to the end fitting as the moveable connector moves along the length of the tube.

17. An apparatus as defined in claim 15, wherein the aperture in the housing is of sufficient size to accept a cartridge placed in fluid communication with the proximal end of the tube upstream of the proximal end of the tube.

18. An apparatus as defined in claim 15 wherein the housing is connected to a source of fluid to be passed through the column.

19. An apparatus for forming a fluid connection with a chromatography column having an end fitting containing a pilot depth with a pilot seat, comprising:
  a housing having a cavity extending through the housing, the cavity having a ledge extending around an interior periphery of the cavity, the cavity having a first end through which fluid passes during use of the apparatus;
  a tubular stem having a proximal end with a flange that cooperates with the ledge to restrain axial motion of the tubular stem relative to the housing along an axial length of the tubular stem in a direction toward a distal end of the tubular stem, the tubular stem having a proximal end extending through a shaped opening in the housing, the proximal end of the tubular stem being in fluid communication with the fluid in the first end of the cavity;
  a movable connector having an aperture through which the distal end of the tubular stem extends a distance sufficient to allow the distal end to be placed against the pilot seat of the pilot depth of the chromatography column to place the tubular stem in fluid communication with the column, the moveable connector being moveable along an axial length of the tubular stem during installation, the moveable connector having a distal end threaded to engage the end fitting on the chromatography column, the moveable connector having a proximal end located in the cavity between the flange and the shaped opening with the proximal end of the moveable connector being configured relative to the shaped opening to permit movement of the moveable connector along the axial length of the stem but restrain rotation about that axial length so the moveable connector and the housing rotate together about that axial length.

20. An apparatus as defined in claim 19, wherein the distal end of the moveable connector has a tapered portion that engages a tapered portion in the end fitting to move the distal end of the moveable connector toward the tubular stem to seal the distal end of the tubular stem to the end fitting as the moveable connector is fastened to the end fitting.

21. An apparatus as defined in claim 19, wherein the cavity in the housing upstream of the flange is configured to accept a cartridge placed in fluid communication with the proximal end of the tubular stem upstream of the proximal end of the tubular stem.

22. An apparatus as defined in claim 21, wherein the cavity in the housing upstream of the flange is configured to accept a cartridge placed in fluid communication with the proximal end of the tubular stem upstream of the proximal end of the tubular stem.

23. An apparatus as defined in claim 19 wherein the a second tube is connected to the cavity to place the cavity in fluid communication with a source of fluid to be passed through the column.

24. A apparatus for use in connecting to a chromatography column having an end fitting containing a pilot depth having a pilot seat, comprising:
  a tube having a longitudinal axis with a distal end configured to abut the pilot seat of the pilot depth and place the tube in fluid communication with the column, the tube having a proximal end extending radially away from a longitudinal axis of the tube;
  a first connector having a seat configured relative to the proximal end of the tube to form a fluid tight seal with the proximal end of the tube and restrain axial motion of the tube in at least one direction along the axis;
  a second connector having a portion configured to engage the end fitting and having an aperture through which the tube extends, the second connector being moveable along the longitudinal axis of the tube relative to the first connector but cooperating with a shaped aperture in the first connector to constrain the first connector and second connector to rotate together about the axis length of the tube.

25. An apparatus as defined in claim 24 wherein the first connector is placed in fluid communication with a source of fluid to be passed through the column, and wherein the axial motion of the tube relative to the first connector along the axis toward the proximal end of the tube is restrained by the first connector.

26. An apparatus for use in connecting to a chromatography column having an end fitting containing a pilot depth having a pilot seat in fluid communication with the column, comprising:

a housing having a cavity extending through the housing;

means for placing the cavity in sealed fluid communication with a proximal end of a tubular stem and restraining motion of a proximal end of the stem relative to the housing along a longitudinal axis of the stem; and means moveable relative to the housing and relative to the longitudinal axis of the stem for connecting a distal end of the stem to the end fitting and placing the distal end of the stem in sealed fluid communication with the pilot seat of the pilot depth, the housing having restriction means cooperating with the moveable means to cause the housing to rotate with the moveable means about the longitudinal axis of the stem.

27. A apparatus as defined in claim 26, wherein the housing further comprises means for containing a cartridge in the housing and placing the cartridge in fluid communication with the stem and the fluid source.

28. A apparatus as defined in claim 26, further comprising means for placing the cavity in fluid communication with a fluid source.

29. A method for forming a fluid connection with a chromatography column having an end fitting containing a pilot depth with a pilot seat in fluid communication with the column, comprising the steps of:

placing a cavity in a housing in sealed fluid communication with a proximal end of a tubular stem, the stem having a longitudinal axis and a distal end;

restraining motion of the proximal end of the stem relative to the housing along the longitudinal axis of the stem in at least one direction;

placing the distal end of the stem against the pilot seat of the pilot depth; moving a connector along the longitudinal axis to connect the distal end of the stem to the end fitting and to seal the distal end of the stem in fluid communication with the pilot seat of the pilot depth; and constraining the connector to rotate with the housing such that rotation of the housing causes the connector to move along the longitudinal axis.

30. A method as defined in claim 29, wherein the step of restraining motion of the proximal end of the stem comprises restraining the motion in the direction toward the proximal end of the stem.

31. A method as defined in claim 29, comprising the further step of placing a cartridge in the cavity intermediate a fluid source and the stem, and in fluid communication with the source and stem.

32. A method as defined in claim 29, comprising the further step of placing the cavity in the housing in fluid communication with a fluid source.

33. A method for forming a fluid connection with a chromatography column having an end fitting containing a pilot depth with a pilot seat in fluid communication with the column, comprising the steps of:

placing a cavity in a housing in sealed fluid communication with a proximal end of a tubular stem;

restraining motion of the proximal end of the stem relative to the housing along a longitudinal axis of the stem in at least one direction;

placing a distal end of the stem against the pilot seat of the pilot depth;

passing the stem through a connector that is constrained to rotate with the housing while moving along the longitudinal axis of the stem;

connecting the distal end of the stem to the end fitting by moving the connector along the longitudinal axis of the tubular stem without moving the distal end of the stem from the pilot seat of the pilot depth.

34. A method as defined in claim 33, wherein the step of restraining motion of the proximal end of the stem comprises restraining the motion in the direction toward the proximal end of the stem.

35. A method as defined in claim 33, comprising the further step of placing a cartridge in the cavity intermediate the fluid source and the stem, and in fluid communication with the source and stem.

36. A method as defined in claim 33, comprising the further step of placing the cavity in fluid communication with a fluid source and passing a liquid through the column.

37. A method as defined in claim 33, comprising the further step of placing the cavity in fluid communication with a fluid source and passing a gas through the column.

38. A method for forming a fluid connection with a chromatography column having an end fitting containing a pilot depth with a pilot seat end in fluid communication with the column, comprising the steps of:

sealing a proximal end of a tubular stem to a first connector adapted to be connected to a chromatography fluid flow path;

restraining movement of the proximal end of the tubular stem along a longitudinal axis of the tubular stem away from the proximal end;

placing a distal end of the stem through a second connector and against the pilot seat of the pilot depth;

connecting the distal end of the stem to the end fitting by rotating the first connector to move the second connector along the longitudinal axis and away from the proximal end of the stem without moving the distal end of the stem from the pilot seat of the pilot depth; and radially compressing a distal end of the second connector to form a seal placing the distal end of the stem in sealed fluid communication with the pilot seat of the pilot depth.

39. A method as defined in claim 38, comprising the further step of placing a cartridge in the cavity intermediate a fluid source and the stem, and in fluid communication with the source and stem.

40. A method as defined in claim 40, comprising the further step of placing the proximal end of the tubular stem in fluid communication with a fluid source and passing a fluid through the column.

41. A connection for use in connecting a fluid inlet to a chromatography column having an end fitting containing a pilot depth having a pilot seat in fluid communication with the column, the connection having a housing with a cavity extending through the housing, comprising:

means cooperating with a tubular stem for restraining motion of the tubular stem relative to the housing at least in one direction along a longitudinal axis of the tubular stem;

means movable relative to the housing and movable along and rotatable about the longitudinal axis of the stem for connecting a distal end of the tubular stem to the end fitting and placing the distal end of the tubular stem in sealed fluid communication with the column and means in the housing for cooperating with the moveable means to cause the moveable means to rotate with the housing about the longitudinal axis of the tubular stem with rotation of the housing causing the movable means to move along the longitudinal axis of the stem.

42. A connection as defined in claim 41, wherein a proximal end of the tubular stem is in fluid communication with the fluid inlet, and wherein the motion of the tubular stem relative to the housing in the direction toward the proximal end of the tubular stem along the longitudinal axis of the tubular stem is restrained.

43. A connection as defined in claim 41, wherein the housing further comprises means for containing a cartridge in the housing and placing the cartridge in fluid communication with the proximal end of the tubular stem and with the fluid inlet.

44. A connector for a chromatography column having an end fitting containing a pilot depth with a pilot seat in fluid communication with the column, comprising:

means in a housing for forming a sealed fluid connection with a fluid inlet;

a tubular stem having a proximal end in the housing and adapted to be placed in fluid communication with the inlet when in use, the stem having a longitudinal axis extending from that proximal end through a distal end of the stem;

means for restraining motion of the stem relative to the housing along the longitudinal axis of the stem;

means movable along, rotatable about and coaxial with the tubular stem for placing the distal end in sealed fluid communication with the column when in use, the housing having means constraining the movable means to rotate with the housing to move along the longitudinal axis of the stem, the stem extending beyond the movable means to form the fluid connection with the inlet.

45. A connector as defined in claim 44, further comprising a cartridge in the cavity in the housing intermediate the fluid inlet and a proximal end of the stem, and in fluid communication with the fluid inlet and the proximal end of the stem.

46. A method for connecting a fluid inlet to a chromatography column having an end fitting, the connection having a housing with a cavity extending through the housing, comprising the steps of:

placing the fluid inlet in sealed fluid communication with a shaped cavity extending through a housing;

engaging a tubular stem in the housing to restrain motion of the tubular stem relative to the housing at least in one direction along a longitudinal axis of the tubular stem and to place the shaped cavity in fluid communication with a proximal end of the stem located in the shaped cavity;

extending the tubular stem to extend through a coaxial connector;

constraining the connector to rotate with the housing so that rotation of the housing causes the connector to move along the longitudinal axis of the stem; and moving the connector relative to the housing and relative to the longitudinal axis of the stem to connect a distal end of the tubular stem to the end fitting and placing the distal end of the tubular stem in sealed fluid communication with the column.

47. The method of claim 46, wherein the step of placing the fluid inlet (490) in sealed fluid communication with a shaped cavity comprises the step of threadingly engaging an end cap having a female fitting, a ferrule seat and the pilot depth, with the housing (420) to seal an end of an inlet tubing against the pilot depth.

48. The method of claim 47, comprising the further step of placing a cartridge in the housing and placing the cartridge in fluid communication with the proximal end (432) of the tubular stem and with the fluid inlet.

49. The method of claim 47, comprising the further step of constraining the motion of the tubular stem relative to the housing in both directions along the longitudinal axis of the stem.

50. A method for forming a fluid connection with a chromatography column (480) having an end fitting containing a pilot depth with a pilot seat in fluid communication with the column, comprising the steps of:

engaging a cavity in a housing with a tubular stem, the stem having a longitudinal axis extending through a distal end and proximal end of the stem;

restraining motion of the stem relative to the housing along the longitudinal axis of the stem in at least one direction;

placing the distal end of the stem against the pilot seat of the pilot depth;

moving a connector along the longitudinal axis to connect the distal end of the stem to the end fitting while constraining the connector to rotate with the housing such that rotation of the housing causes the connector to move along the longitudinal axis, and sealing the distal end of the stem in fluid communication with the pilot seat of the pilot depth.

51. A method according to claim 50, wherein the step of restraining motion of the stem along the longitudinal axis comprises the step of restraining the motion in the direction toward the proximal end of the stem.

* * * * *